United States Patent [19]

Mobilio et al.

[11] Patent Number: 5,438,064

[45] Date of Patent: Aug. 1, 1995

[54] DERIVATIVES OF 4-ANILINOQUINOLINE-3-CARBOXAMIDE AS ANALGESIC AGENTS

[75] Inventors: Dominick Mobilio, Somerset; Albert J. Molinari, Princeton, both of N.J.

[73] Assignee: American Home Products Corporation, Madison, N.J.

[21] Appl. No.: 812,791

[22] Filed: Dec. 23, 1991

[51] Int. Cl.$^6$ .................. C07D 215/46; A61K 31/47
[52] U.S. Cl. ..................... 514/313; 546/162
[58] Field of Search ......... 546/162; 514/313

[56] References Cited

U.S. PATENT DOCUMENTS

| 1,747,531 | 2/1930 | Schulemann | 546/162 |
|---|---|---|---|
| 3,647,802 | 3/1972 | Carney | 546/162 |
| 3,875,165 | 4/1975 | Archibald | 546/161 |
| 3,933,829 | 1/1976 | Archibald | 546/160 |
| 3,971,787 | 7/1976 | Archibald | 546/161 |
| 3,971,789 | 7/1976 | Archibald | 546/161 |
| 4,167,567 | 9/1979 | McCall | 514/253 |
| 4,357,333 | 11/1982 | Archibald | 514/313 |
| 4,666,924 | 5/1987 | Stout | 514/343 |
| 4,839,369 | 6/1989 | Youssefyeh | 514/314 |

FOREIGN PATENT DOCUMENTS 230718A  2/1985  European Pat. Off. .
309043A  9/1987  European Pat. Off. .

Primary Examiner—Johann Richter
Assistant Examiner—Catherine S. Kilby Scalzo
Attorney, Agent, or Firm—R. F. Boswell, Jr.

[57] ABSTRACT

Derivatives of 4-anilinoquinoline having the formula:

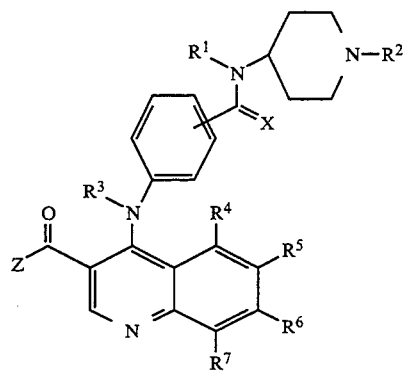

where X is O or $H_2$ and Z is 1-substituted-4-piperidinylamino or diloweralkylaminoloweralkyl inhibit binding of tritiated bradykinin to guinea pig ileum and inhibit bradykinin-induced writhing in mice. Bradykinin is a nonapeptide formed in plasma as a result of inflammation or injury and produces pain when it binds with pain receptors. A drug which inhibits the binding of bradykinin therefore has analgetic properties.

21 Claims, No Drawings

DERIVATIVES OF 4-ANILINOQUINOLINE-3-CARBOXAMIDE AS ANALGESIC AGENTS

BACKGROUND OF THE INVENTION

1. Field of Invention

This invention relates to derivatives of 4-anilinoquinoline-3-carboxamide which have analgetic properties as determined *in vitro* by competitive antagonism of tritiated bradykinin binding to guinea pig ileum.

This invention further relates to a method for reducing pain and to a pharmaceutical composition comprising an invention compound and a pharmaceutical carrier.

2. Information Disclosure Statement

U.S. Pat. No. 3,362,954 describes compounds of the formula below for which antiinflammatory activity is claimed.

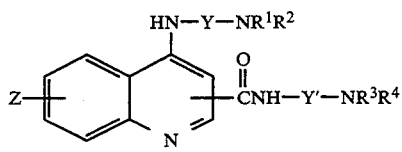

In the above formula, Y and $Y^1$ are $C_1$–$C_6$ alkylene; —$NR^1R^2$ and —$NR^3R^4$ are dialkylamino, N-alkyl-N-hydroxyalkylamino, piperidine, alkylated piperidine, pyrrolidine, alkylated pyrrolidine, or morpholine; and Z is one or more of: halogen, alkyl, alkoxy, alkylmercapto, alkanoylamino, alkylamino, amino, nitro, hydroxy, alkanoyloxy, benzyloxy, or trihalomethyl.

A 4-anilinophthalazine having antiarrhythmic and antimalaria properties as shown in the following structure was described in U.S. Pat. No. 4,666,924.

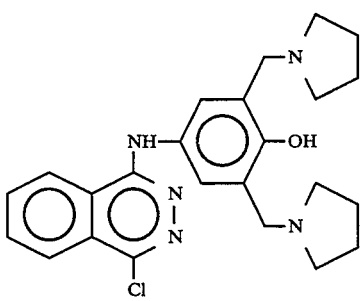

European Patents 230-718A and 309-043A describe arylcarboxamides having gastric prokinetic utility of the formula:

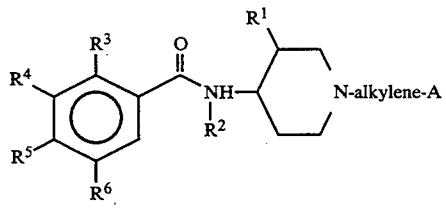

where $R^1$ is H or OH, $R^2$ is H or $C_1$–$C_6$ alkyl, $R^3$–$R^6$ are H, $C_1$–$C_6$ alkyl, $C_1$–$C_6$ alkoxy, halo, etc., and A is OH, carboxy, a heterocycle, etc.

SUMMARY OF THE INVENTION

The compounds of this invention are represented by Formula I below or a pharmaceutically acceptable salt thereof.

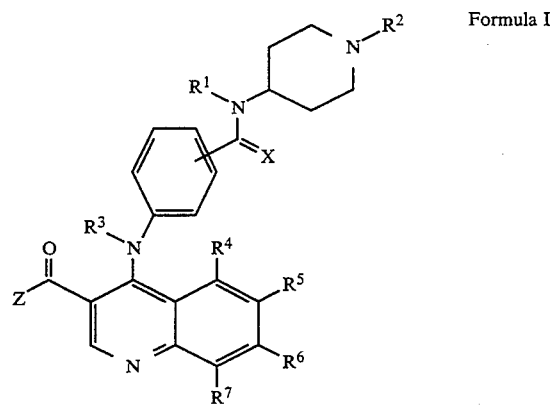

Formula I

Under Formula I,
X=O or $H_2$;
$R^1$=H when X=O, or H or $R^{15}CO$ when X=$H_2$;
$R^2$=lower alkyl, cycloalkyl, —$(CH_2)_m$-cycloalkyl, —$(CH_2)_m CONR^3R^3$,

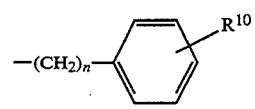

m is 1 to 10 and n is 1 to 4;
$R^3$=H or lower alkyl;
$R^4$, $R^5$, $R^6$ and $R^7$ are independently H, lower alkyl, fluoro, chloro, bromo, iodo, lower alkoxy, or perfluorolower alkyl;
Z=$R^8N$—$R^{17}$ where $R^{17}$ is

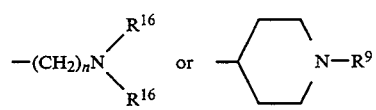

wherein
$R^8$=H, or $R^{16}$ wherein $R^{16}$ is lower alkyl and
$R^9$=lower alkyl,

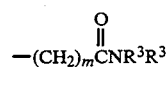

or

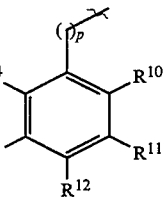

and n and p are independently=1 to 4 and m is 1 to 10; $R^{10}$, $R^{11}$, $R^{12}$, $R^{13}$ and $R^{14}$ are independently H, lower alkyl, fluoro, chloro, bromo, iodo, lower alkoxy, perfluorolower alkyl, —CONR$^{16}$R$^{16}$, —CONHR$^{16}$, —CONH$_2$, NO$_2$, OH, NH$_2$, —NHCONH$_2$, —NR$^3$CONR$^3$R$^3$, or —SO$_y$R$^{16}$ wherein y=0, 1 or 2, R$^{15}$=H, lower alkyl, phenyl, phenylalkyl, perfluorolower alkyl, or —(CH$_2$)$_m$ cycloalkyl.

In the above definitions, lower alkyl is a straight or branched hydrocarbon chain of from 1-6 carbons such as methyl, ethyl, propyl, isopropyl, butyl, t-butyl and hexyl. Lower alkoxy means —O—(lower alkyl). Cycloalkyl includes cyclic hydrocarbons of from 3 to 6 carbons. The terms arylalkyl and phenylalkyl refer to a loweralkyl group to which a phenyl group is attached. Perfluorolower alkyl refers to a lower alkyl group where all the hydrogen atoms are replaced with fluorine atoms. Where the same variable, i.e., R$^3$, R$^{16}$ or m, appears more than once in a formula, each group is selected independently of the other.

The preferred compounds of this invention or a pharmaceutically acceptable salt thereof are those of Formula II below.

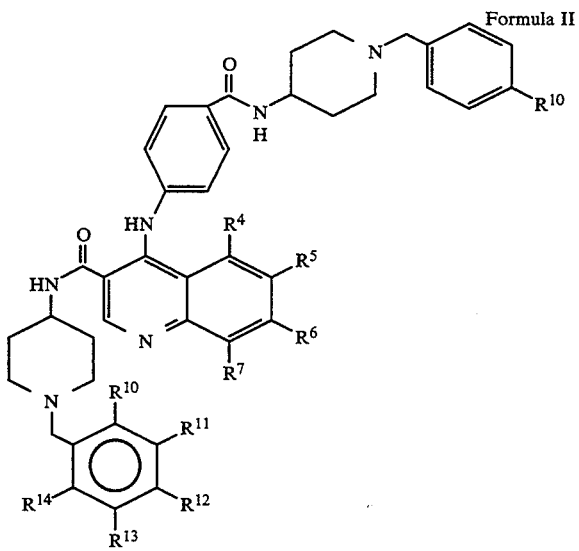

Formula II wherein the variables R$^4$, R$^5$, R$^6$, R$^7$, R$^{10}$, R$^{11}$, R$^{12}$, R$^{13}$ and R$^{14}$ are as defined under Formula I.

The term pharmaceutically acceptable salt encompasses the acid addition salts, hydrates or other solvates. The acid addition salts are formed from pharmacologically acceptable organic and inorganic acids such as hydrochloric, hydrobromic, sulfonic, sulfuric, phosphoric, nitric, maleic, fumaric, benzoic, ascorbic, pamoic, suetinit, methansulfonic, acetic, propionic, tartaric, citric, lactic, malic, mandelic, cinnamic, palmitic, itaconic, and benzensulfonic acids.

The compounds of this invention bind competitively with bradykinin at pain receptor sites and thus are useful in a method of treating pain. The compounds of this invention are also useful in a pharmaceutical composition for treating pain.

Bradykinin is a nonapeptide that is formed in the plasma from alpha-2-globulins in response to certain stimuli such as tissue damage resulting from injury or inflammation and binds to pain receptors at the nerve ending thus evoking pain. Bradykinin is known to produce intense pain when applied to a blister base on man, causes writhing when administered intraperitoneally in rats and mice, and, among other pharmacological responses causes a slow contraction in guinea pig ileum.

A bradykinin antagonist binds competitively with bradykinin at pain receptor sites and thus inhibits the pain resulting from response to bradykinin. Since bradykinin also binds with guinea pig ileum, the ability of a drug molecule to inhibit binding of $^3$H-bradykinin is taken as a determination of analgetic activity. Such determination can be made in vitro using isolated tissue from the guinea pig ileum. The compounds of the present invention inhibit 50% of the bradykinin binding at concentrations of from about 0.08 to 12 μM. Several of the compounds were tested in the in vivo writhing assay in which the effects of a test compound on bradykinininduced writhing in mice is determined.

DETAILED DESCRIPTION OF THE INVENTION

The analgetic compounds of Formula I are prepared from ethyl 4-chloroquinoline-3-carboxylate and analogs (1) as shown in the following reaction schemes. The variable R groups shown in the following schemes are as defined hereinabove.

Scheme 1. Preparation of compounds of Formula I where X is O.

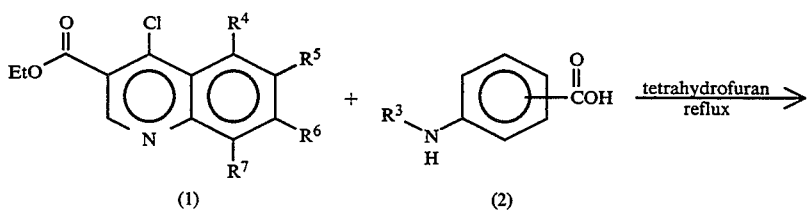

-continued
Scheme 1. Preparation of compounds of Formula I where X is O.
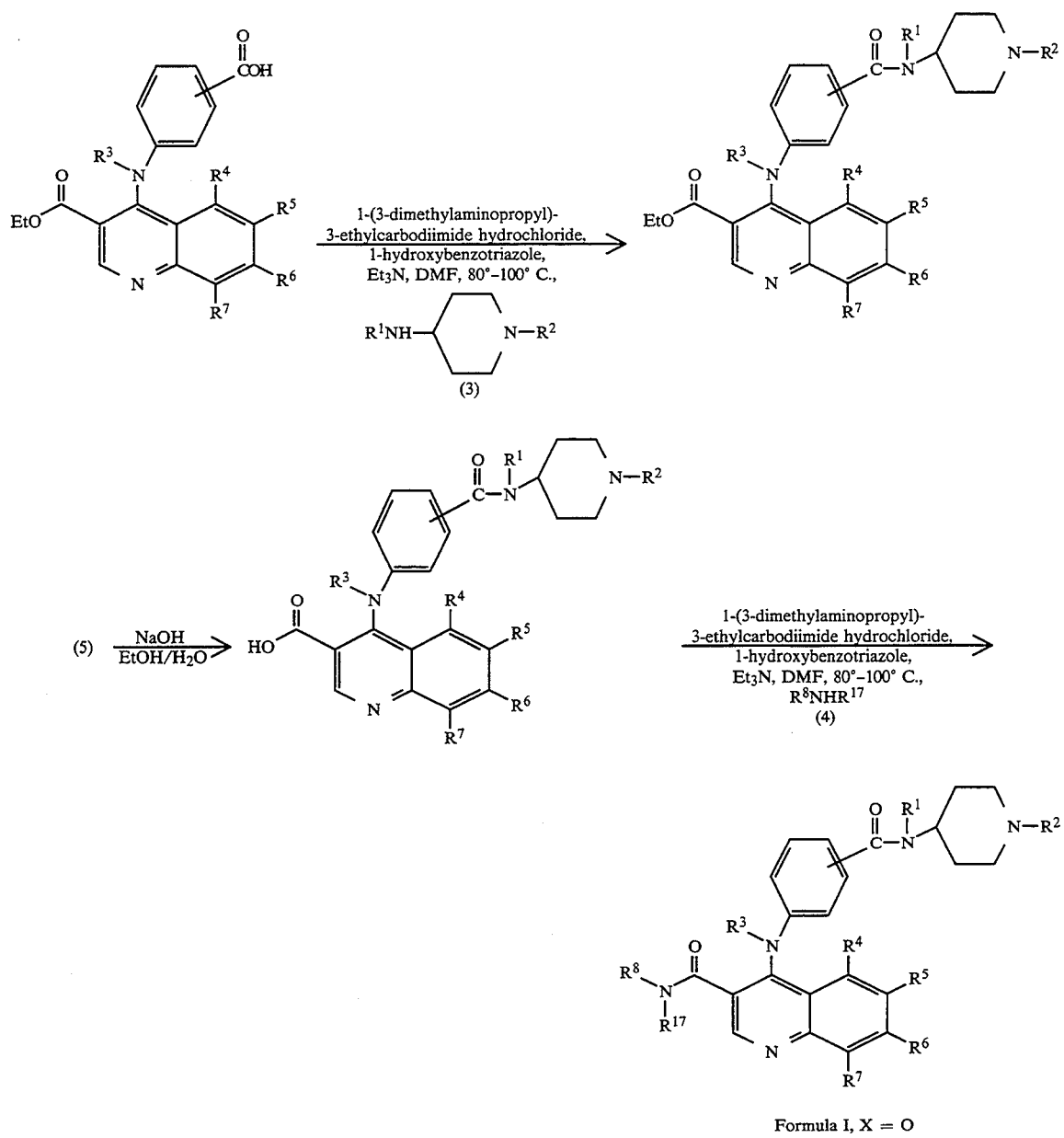
Scheme 2. Preparation of Formula I compounds where X is H₂
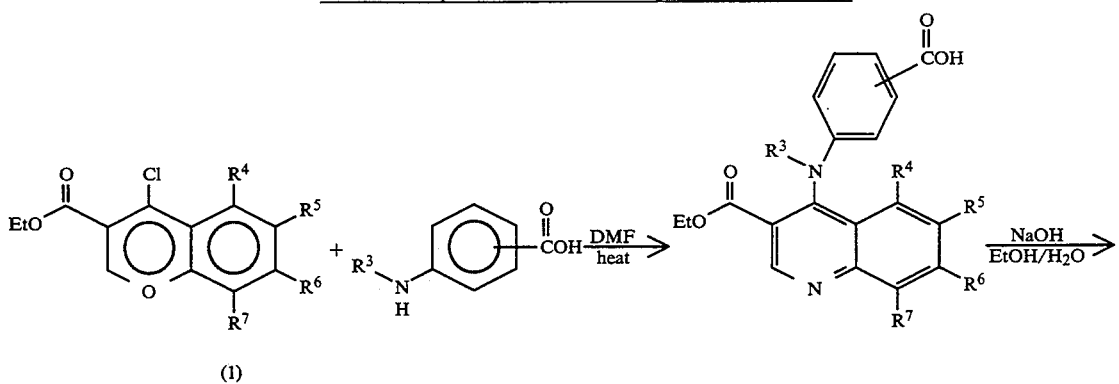

-continued
Scheme 2. Preparation of Formula I compounds where X is H$_2$

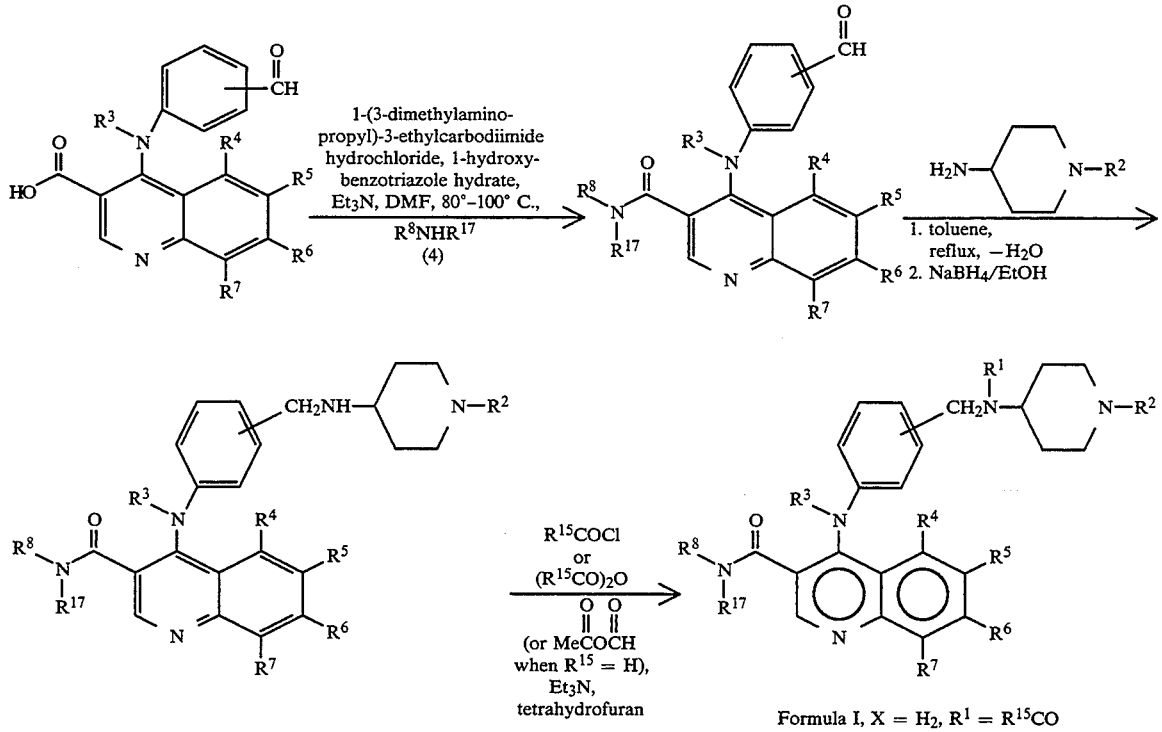

Formula I, X = H$_2$, R$^1$ = R$^{15}$CO

The intermediates (1) are prepared according to the procedures described in J. Amer Chem. Soc. 68, 1204 (1946). Ethoxymethylenemalonate is warmed with an appropriate aniline to give an anil which cyclizes upon heating in boiling diphenylether to give the ethyl-4-hydroxyquinoline-3-carboxylate. Reaction of this intermediate with phosphorus oxychloride gives the intermediate (1). The intermediates (2) are either commercially available or can be prepared from the corresponding ester by hydrolysis. The intermediate (3) can be prepared from (6) by

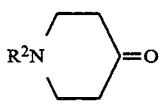
(6)

treatment with hydroxylamine hydrochloride followed by reduction of the oxime with nickle/aluminum alloy as described in U.S. Pat. No. 3,875,163, or, when a weaker reducing agent is required, by treatment with ammonium acetate followed by reduction with sodium cyanoborohydride as described in J. Amer. Chem. Soc., 68, 7032 (1979). The intermediate (6) can be prepared. as described in U.S. Pat. No. 4,816,464. The intermediate R$^8$NHR$^{17}$ where R$^{17}$ is

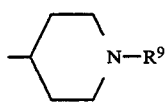

and R$^8$ is not H can be prepared from (3) by acylation with R$^{15}$COCl or (R$^{15}$CO)$_2$O or formylation with formic acetic anhydride followed by reduction with lithium aluminum hydride.

The following specific examples illustrate methods for preparation of compounds of this invention.

EXAMPLE 1

N-[1-[4-(1,1-Dimethylethyl)phenyl]methyl-4-piperidinyl]-8-methoxy -4-[[4-[[[1-(phenylmethyl) -4-piperidinyl]amino]carbonyl]phenyl]amino]-3-quinolinecarboxamide N-[1-[4-( 1,1-Dimethylethyl)pheny]]methyl]-4-piperidinyl]]-8-methoxy-4-[[4-[[[1-(phenylmethyl)-4-piperidinyl]amino]carbonyl]phenyl]amino]-3-quinoline-carbox-amide was prepared as a hygroscopic solid (0.2 hydrate) by coupling 8-methoxy-4-[[4-[[[1-(phenylme-thyl)-4-piperidinyl]amino]carbonyl]phenyl]amino]-3-quinoline-carboxylic acid and 1-[[4-(1,1-dimethylethyl)-phenyl]methyl]-4piperidinamine as described for Example 17, Step 5. 8-Methoxy-4-[[4-[[[1-(phenylmethyl)-4-piperi-dinyl]amino]carbonyl]phenyl]amino]-3-quinolinecarboxylic acid can be prepared as described for 7-chloro-4-[[4-[[[1-(phenylmethyl)-4-piperidinyl-]amino]carbonyl]phenyl]amino]-3-quinolinecarboxylic acid in Example 17, Steps 1–4, by starting with 1,4-dihydro-8-methoxy-4-oxo-3-quinolinecarboxylic acid ethyl ester in Step 1. 1,4-Dihydro-8-methoxy-4-oxo-3-quinolinecarboxylic acid ethyl ester can be prepared as described by C. C. Price et al in J. Am. Chem. Soc., 68, 1204 (1946). 1-[[4-(1,1-Dimethylethyl)phenyl]methyl]-4-piperidinamine can be prepared from 4-(tert-butyl)-benzyl bromide and 1,4-dioxa-8-azaspiro[4.5]-decane as described in U.S. Pat. Nos. 3,875,165 and 4,816,464: mp 154°–162 ° C.; $^1$H NMR (Me$_2$SO-d$_6$, 400 MHz) δ9.47 (s, 1 H), 8.76 (s, 1 H), 8.39 (d, J=7.5 Hz, 1 H), 7.99 (d, J=7.6 Hz, 1 H), 7.68 (d, J=8.7 Hz, 2 H), 7.57 (d, jr=8.3 Hz, 1 H), 7.41 (m, 1 H), 7.10–7.36 (m, 10 H), 6.87 (d, J=8.7 Hz, 2 H), 3.95 (s, 3 H), 3.7 (m, 1 H), 3.2–3.6 (m, 5 H), 2.6–2.9 (m, 4 H), 1.8–2.1 (m, 4 H), 1.3–1.8 (m, 3 H), 1.24 (s, 9 H); Karl Fisher, 0.47% H$_2$O.

Anal. Calcd for $C_{46}H_{54}N_6O_3 \cdot 0.2 H_2O$: C, 74.41; H, 7.38; N, 11.32
Found: C, 73.80; H, 7.21; N, 11.30

EXAMPLE 2

N-[1-[(3-chloronhenyl)methyl]-4-piperidinyl]-8-methoxy-4-[[4-[[[1-(phenylmethyl) -4-piperidinyl]amino]carbonyl]phenyl]amino]-3-quinolinecarboxamide N-[1-[(3-Chlorophenyl)methyl]-4-piperidinyl]-8-methoxy-4-[[4-[[[1-(phenyl-methyl -4-piperidinyl]amino]carbonyl]phenyl]amino]-3-quinoline-carboxamide was prepared as a hygroscopic solid (0.04 hydrate) by coupling 8-methoxy-4-[[4-[[[1-(phenylmethyl) -4-piperidinyl]amino]carbonyl]phenyl]amino]-3-quinolinecarboxylic acid and 1-[(4-chlorophenyl)methyl]-4-piperidinamine as described for Example 17, Step 5. 1-[(4-Chlorophenyl)methyl]-4-piperidinamine can be prepared from 3-chlorobenzyl chloride and 1,4-dioxa-8-azaspiro[4.5]-decane as described in U.S. Pat. No. 4,816,464 and J. Amer. Chem. Soc., 68, 7032 (1979): mp 164°–168 ° C.; $^1H$ NMR (Me$_2$SO-d$_6$, 400 MHz) δd 9.49 (s, 1 H), 8.77 (s, 1 H), 8.40 (d, J=7.6 Hz, 1 H), 7.99 (d, J=7.8 Hz, 1 H), 7.69 (d, J=8.7 Hz, 2 H), 7.58 (d, J=8.1 Hz, 1 H), 7.41 (m, $^1H$), 7.15–7.35 (m, 10 H), 6.88 (d, J=8.7 Hz, 2 H), 3.94 (s, 3 H), 3.65–3.80 (m, 1 H), 3.3–3.6 (m, 5 H), 2.6–2.9 (m, 4 H), 1.85–2.05 (m, 4 H), 1.62–1.80 (m, 2 H), 1.2–1.6 (m, 6 H); Karl Fischer, 0.089% H$_2$O.
Anal. Calcd for $C_{42}H_{45}ClN_6O_3 \cdot 0.04 H_2O$: C, 70.26; H, 6.33; N, 11.71
Found: C, 68.83; H, 6.22; N, 11.21.

EXAMPLE 3

8-Methoxy-N-[1-(phenylmethyl)-4-piperidinyl[-4-[[4-[[[1-(phenylmethyl)-4-piperidinyl]amino]carbonyl]phenylamino]-3-quinolinecarboxamide 8-Methoxy-N-[1-(phenylmethyl)-4-piperidinyl]-4.-[[4-[[[1-(phenylmethyl)-4-piperidin]amino]carbonyl]phenyl]amino]-3-quinolinecarboxamide was prepared by coupling 8-methoxy-4-[[4-[[[1-(phenylmethyl)-4-piperidinyl]amino]carbonyl]phenyl]amino]-3-quinolinecarboxylic acid and commercially available 4-amino-1-benzylpiperidine as described for Example 17, Step 5: mp 196°–199 ° C.; $^1H$ NMR (Me$_2$SO-d$_6$, 400 MHz) δ 9.47 (s, 1 H), 8.76 (s, 1 H), 8.38 (d, J=7.5 Hz, 1 H), 7.97 (d, J=8.0 Hz, 1 H), 7.68 (d, J=8.5 Hz, 2 H), 7.58 (d, 8.6 Hz, 1 H), 7.41 (t, J=8.2 Hz, 1 H), 7.25 (m, 10 H), 7.19 (d, J=7.9 Hz, 1 H), 6.87 (d, J=8.6 Hz, 2 H), 3.95 (s, 3 H), 3.73 (m, 1 H), 3.48 (m, 1 H), 3.44 (s, 2 H), 3.37 (s, 2 H), 2.78 (d, J=11.0 Hz, 2 H), 2.67 (d, J=11.6 Hz, 2 H), 1.98 (t, J=10.6 Hz, 2 H), 1.89 (t, J=10.0 Hz, 2 H), 1.68 (d, J=9.7 Hz, 2 H), 1.53 (m, 4 H), 1.36 (q, J=11.2 Hz, 2 H).
Anal. Calcd for $C_{42}H_{46}N_6O_3 \cdot 0.17 CH_2Cl_2$: C, 72.64; H, 6.70; N, 12.05
Found: C, 72.53; H, 6.90; N, 12.13

EXAMPLE 4

N-[2-(Dimethylamino)ethyl]-8-methoxy-4-[[4- [[[1-(phenylmethyl) -4-piperidinyl]amino]carbonyl]phenyl]amino]-3-quinolinecarboxamide trifluoroacetate (1:4) was prepared by coupling 8-methosy-4-[[4-[[[1-(phenylmethyl) -4-piperidinyl]amino]carbonyl]phenyl] amino]-3-quinolinecarboxylic acid and commercially available N,N-dimethylethylenediamine as described for Example 17, Step 5. The compound is purified by reverse phase HPLC on C$_{18}$ silica gel (gradient elution from 0.1% trifluoroacetic acid in 5% MeCN/H$_2$O to 100% MeCN). This afforded the product as tetra-trifluroacetate salt after concentrating the fractions from the HPLC run: mp 113°–16° C.; $^1H$ NMR (Me$_2$SO-d$_6$, 400 MHz) δ 10.99 (bs, 1H), 10.06 (bs, 1 H), 9.95 (bs, 1H), 9.78 (bs, 1 H), 8.98 (bt, 1 H), 8.67 (s, $^1Ha$), 8.65 (s, $^1Hb$), 8.54 (d, J=7.3 Hz, 1Hb), 8.40 (d, J=5.7Hz, 1Ha), 8.02 (d, J=8.0 Hz, 1 H), 7.91 (d, J=7.5 Hz, 2Ha), 7.86 (d, J=8.6, 2Hb), 7.68 (t, J=8.2 Hz, 1 H), 7.57 (d, J=8.2 Hz, 1 H), 7.48 (m, 5 H), 7.24 (d, J=8.3 Hz, 2 H), 4.35 (d, J=3.6 Hz, 2Ha), 4.29 (d, J=3.6 Hz, 2Hb), 4.10 (s, 3 H), 3.97 (m, 1 H), 3.76 (bs), 3.40 (d, J=10.8 Hz, 2 H), 3.27 (bs), 3.08 (m, 4 H), 2.91 (bm, 2 H), 2.73 (s, 6 H), 2.02 (d, J=13.2 Hz, 2 H), 1.78 (q, J=11.9 Hz, 2 H).
Anal. Calcd for $C_{42}H_{44}F_{12}N_6O_{11}$: C, 48.65; H, 4.27; N, 8.10.
Found: $C_{34}H_{36}N_6O_3 \cdot 4C_3H_3F_3O_2$ C, 49.30; H, 5.00; N, 8.44.

EXAMPLE 5

N-[2-(Dimethylamino)ethyl]-N-ethyl-8-methoxy-4-[[4-[[[1-(phenylmethyl) -4-piperidinyl]amino]carbonyl]phenyl]amino]-3-quinolinecarboxamide N-[2-(Dimethylamino)ethyl]-N-ethyl-8-methoxy-4-[[4-[[[1-(phenylmethyl)-4-piperidinyl]amino]carbonyl]phenyl]amino]-3-quinolinecarboxamide was prepared by coupling 8-methoxy-4-[[4-[[[1-(phenylmethyl)-4-piperidinyl]amino]carbonyl]phenyl]amino]-3-quinolinecarboxylic acid and commercially available N,N-dimethyl-N'-ethylethylenediamine as described for Example 17, Step 5. The compound is purified by reverse phase HPLC on C$_{18}$ silica gel (gradient elution from 0.1% trifluoroacetic acid in 5% MeCN/H$_2$O to 100% MeCN). Neutralization of the trifluoroacetate salt after concentrating the fractions from the HPLC run afforded the title compound as an amorphous solid that was triturated in ether: mp 120°–123 ° C.; $^1H$ NMR (Me$_2$SO-d$_6$, 400 MHz), 1:1 mixture of amide rotamers, a: b) δ 9.00 (s, 1Ha), 8.94 (s, 1Hb), 8.54 (s, 1Ha), 8.51 (s, 1Hb), 7.99 (d, J=7.9 Hz, 1Hb), 7.96 (d, J=8.1 Hz, 1Ha), 7.73 (d, J=8.5 Hz, 2Hb), 7.69 (m, 2Ha, 1 H), 7.49 (t, J=8.1 Hz, 1 H), 7.30 (m, 5 H), 7.26 (d, J=8.3 Hz, 1 H), 6.89 (d, J=8.7 Hz, 2Hb), 6.85 (d, J=8.5 Hz, 2Ha), 3.96 (s, 3 H), 3.74(m, 1 H), 3.46(s, 2H),3.11 (m, 4H),2.80(d,J=10.4Hz, 2H),2.18(t,J=5.6 Hz, 2Hb), 2.02 (m, 2 H), 1.99 (s, 6Hb), 1.83 (s, 6Ha), 1.70 (m, 2 H, 2Ha), 1.56 (qd, J=10.8, 3.6Hz, 2 H), 0.91 (t, J=6.9 Hz, 3Hb), 0.61 (t, J=6.9 Hz, 3Ha).
Anal. Calcd for $C_{36}H_{44}N_6O_3$: C, 71.03; H, 7.28; N, 13.80
Found: C, 69.44; H, 7.28; N, 13.12

EXAMPLE 6

4-[[4-[[[(3-Cyclopentyl-1-oxopropyl)[1-[6-(diethylamino)-6-oxohexyl -4-piperidinylamino]methylphenyl]amino]-8-methoxy-N-[1-(phenylmethyl) -4-piperidinyl-3-quinolinecarboxamide Step 1, 4-[(4-Formylphenyl)amino]-8-methoxy-3-quinoline-carboxylic acid ethyl ester: 4-Chloro-8-methoxy-3-quinolinecarboxylic acid ethyl ester (10.62 g, 40 mmol) and 4-aminobenzaldehyde (4.85 g, 40 mmol) were suspended in dry DMF (100 mL) and treated dropwise with concentrated HCl (aq) (3.3. mL, 40 mmol). The mixture was heated at 90° C. for 40 min. After dilution with methylene chloride (800 mL) the reaction mixture was extracted with 1N NaOH (200 mL) and water (3×200 mL) and the dried (MgSO$_4$) organic phase evaporated to a yellow oil. Crystallization from a minimum amount of ether afforded 8.0 g (22.8 mmol), 57% yield) of the product as a light yellow solid: m.p. 108°–110° C. (dec): $^1$H NMR (Me$_2$SO-d$_6$, 400 MHz) δ 9.79 (s, 1 H), 9.70 (s, 1 H), 8.99 (s, 1 H), 7.75 (d, J=8.7 Hz, 2 H), 7.64 (d, J=7.9 Hz, 1 H), 7.52 (t, J=7.9 Hz, 1 H), 7.31 (d, J=7.9 Hz, 1 H), 7.01 (d, J=8.5 Hz, 2 H), 4.02 (q, J=7.1 Hz, 2 H), 3.99 (s, 3 H), 1.08 (t,J=7.1 Hz, 3 H); MS(EI), m/z (rel. intensity)=350 (M+, 100), 321(34), 275(68), 247(58), 218(35), 205(18), 190(21); IR(KBr) 3430, 3350, 2820, 2740, 1685, 1590, 1500, 1390, 1270, 1215, 1160, 1060, 1020, 770cm$^{-1}$.
Anal. Calcd. for C$_{20}$H$_{18}$N$_2$O$_4$: C, 68.56; H, 5.18; N, 8.00 Found: C, 68.06; H, 4.95; N, 7.74.

Step 2, 4-[[4-[[[1-[6-(Diethylamino)-6-oxohexyl]-4-piperidinyl]-amino]-methyl]phenyl]amino]-8-methoxy-3-quinolinecarboxylic acid methyl ester: A mixture of 4-[(4-formylphenyl)amino]-8-methoxy-3-quinoline-carboxylic acid ethyl ester hydrochloride (7.75 g, 20 mmol) [converted to the hydrochloride salt by treatment of the free base with hydrogen chloride (g) in ether, followed by filtration], N,N-diethyl 6-(4-amino-1-piperidinyl)hexanamide (5.66 g, 20 mmol), and 4-toluenesulfonic acid monohydrate (1.90 g, 10 mmol) was refluxed in toluene (500 mL) for 1 hour with azotropic removal of water. A second aliquot of 4toleuenesulfonic acid monohydrate (1.90 g, 10 mmol) was added and azotropic refluxing continued for 2 hours. The solvent was removed in vacuo, and the residue (20 g) redissolved in methanol. The stirred solution was treated with an excess of sodium borohydride at room temperature. The solvent was removed in vacuo, the residue redissolved in methylene chloride and extracted with 1N NaOH (aq) and water (2X). The dried (MgSO$_4$) organic phase was evaporated to a crude oil (9.2 g). The product was purified by flash column chromatography on silica gel (100:1 loading ratio with gradient elution, 5–10% methanol-methylene chloride saturated with ammonia gas) and afforded 2.0 g (3.3 mmol, 17% yield) of an amber oil, the methyl ester of the title compound (due to ester exchange): $^1$H NMR (Me$_2$SO-d$_6$, 400 MHz), 1:1 Mixture of amide rotamers, a:b) δδ 9.65 (s, 1 H), 8.90 (s, 1 H), 7.48 (d, J=8.7 Hz, 1 H), 7.32 (t, J=7.9 Hz, 1 H), 7.28 (d, J=8.3 Hz, 2 H), 7.20 (d, J=7.7 Hz, 1 H), 6.97 (d, J=8.5 Hz, 2 H), 3.94 (s, 3 H), 3.62 (s, 3 H), 3.28 (bm, 4 H), 3.27 (q,J =7.1 Hz, 2Ha), 3.23 (q, J=7.1 Hz, 2Hb), 2.84 (d, J=10.2 Hz, 2 H), 2.28 (m, 2 H), 2.22 (t, J=7.3 Hz, 2 H), 1.91 (bm, 2 H), 1.84 (d, J=11.4 Hz, 2 H), 1.48 (p, J =7.7 Hz, 2 H), 1.40 (m, 4 H), 1.24 (p, J=7.3 Hz, 2 H), 1.08 (t, J=7.1 Hz, 3Ha), 0.98 (t,J =7.1 Hz, 3Hb); MS(+FAB), m/z (rel. intensity)=604 (MH+, 20), 590 (MH+, 25); IR(KBr) 3420, 2920, 1680, 1635, 1505, 1270, 1205, 1055, 1005, 775 cm$^{-1}$.
Anal. Calcd. for C$_{34}$H$_{47}$N$_5$O$_4$: C, 69.24; H, 8.03; N, 11.87
Found: C, 66.49; H, 7.53; N, 11.23

Step 3, 4-[[4-[[(3-Cyclopenty-1-oxopropyl)[1-[6-(diethylamino)-6-oxohexyl]-4-piperidinyl]amino]methyl]-phenyl]amino]-8-methoxy-3-quinolinecarboxylic acid: A mixture of 4-[[4-[[[1-[6-(diethylamino)-6-oxohexyl]-4-piperidinyl]amino]-methyl]phenyl]amino]-8-methoxy-3-quinolinecarboxylic acid methyl ester (2.0 g, 3.3 mmol) and triethylamine (0.33 g, 3.3 mmol), dissolved in dry THF (50 mL), was treated dropwise with 3-cyclopentylpropionyl chloride (0.53 g, 3.3 mmol) under nitrogen at room temperature and stirred for 1 hour. After diluting with methylene chloride, the reaction mixture was extracted with 1N NaOH (aq) and water. The dried (MgSO$_4$) organic phase was concentrated to an oil, redissolved in methanol (50 mL), and treated with 2.5N NaOH (aq) (10 mL, 25 mmol). The mixture was refluxed for 2 hours. Neutralization with 2N HCl (aq) (12.5 mL, 25 mmol) afforded, after filtration of the chilled precipitate, 2.1 g (3.0 mmol, 91% yield) of the free acid as a yellow solid.

Step 4, 4-[[4-[[(3-Cyclopentyl-1-oxopropyl)[1-[6-(diethylamino)-6-oxohexyl]-4-piperidinylamino]methyl]-phenyl]amino]-8-methoxy-N-[1-(phenylmethyl) -4-piperidinyl]-3-quinolinecarboxamide tetrahydro-chloride: A mixture of 4-[[4-[[(3-cyclopentyl-1-oxopropyl)[1-[6-(diethylamino)-6-oxohexyl]-4-piperidinyl]amino]methyl]phenyl]amino]-8-methoxy-3-quinolinecarboxy-lic acid (2.1 g, 3.0 mmol), 1-(3-dimethylaminopropyl)-3-ethylcarbodiimide hydrochloride (0.96 g, 5.0 mmol), 1-hydroxybenzotriazole monohydrate (0.47 g, 3.5 mmol), triethylamine (1.01 g, 10.0 mmol), and 4-amino-1-benzylpiperidine (0.57 g, 3.0 mmol) was suspended in dry DMF (60 mL) and heated at 60° C. for 4 hours under nitrogen. After dilution with methylene chloride, the reaction mixture was extracted with 1N NaOH (aq) (200 mL) and water (3×75 mL). The dried (MgSO$_4$) organic phase was evaporated in vacuo to an amber oil. The product was purified by flash column chromatography on silica gel (100:1 loading ratio; methylene chloride/methanol sat. ammonia gas, 90/10 eluant) which afforded 2.0 g (2.3 mmol, 77% yield) of the purified free base as an amber oil. Conversion to the tetrahydrochloride salt with hydrogen chloride (g) in ethanol-ether afforded, after drying in vacuoovernight (6 hours at 110° C.), 1.75 g (1.72 mmol, 57% yield) of the title compound as a yellow amorphous solid: m.p. 160°–165° C.; $^1$H NMR (Me$_2$SO-d$_6$, 400 MHz) 15 14.11 (bm), 11.20 (bm), 9.28 (bm), 8.87 (d, J=5.6 Hz), 8.84 (d, J=6.9 Hz), 8.41 (s), 8.37 (bm), 7.67 (d, J=8.4 Hz), 7.64 (bin), 7.59 (bm), 7.42 (bm), 7.24 (m), 7.14 (s), 4.80 (bin), 4.49 (bm), 4.36 (d), 4.28 (d), 4.09 (s), 3.52 (m), 3.24 (m), 3.00 (m), 2.25 (m), 2.04 (t), 1.75 (bm), 1.48 (bm), 1.28 (p), 1.17 (m), 0.98 (m); MS (+FAB), m/z (rel. intensity)=872 (MH+, 50); IR (KBr) 3420, 2930, 1630, 1560, 1420, 1275, 1210, 1180, 1060, 750, 700 cm$^{-1}$; Ionic Halogen Calcd. for Cl$_4$: 13.98. Found: 13.21.
Anal. Calcd. for C$_{52}$H$_{73}$N$_7$O$_4$.4HCl: C, 62.53; H, 7.62; N, 9.63
Found: C, 61.65; H, 7.95; N, 9.35.

EXAMPLE 7

4-[[4-[[( 1-Butyl-4-piperidinyDamino]methyl]-phenylamino]-8-methoxy-N-[1-(phenylmethyl)-4-piperidinyl]-3-quinolinecarboxamide Step 1, 4-[(4-Formylphenyl)amino]-8-methoxy-3-quinolinecarboxylic acid: 4-[(4-Formylphcnyl)amino]-8-methoxy-3-quinolinccarboxylic acid ethyl ester (7.0 g, 20 mmol) and 2.5N NaOH (aq) (20 mL, 50 mmol) were refluxed for 1 hour in MeOH (150 mL). Concentration of the reaction mixture, neutcalization with concentrated HCl (4.13 mL, 50 mmol), and filtration afforded 5.4 g (16.8 mmol, 84% yield) of the free acid as a yellow powder which was air-dried overnight: m.p. (100) 130° C. (dec). Step 2, 4-[(4-Formylphenyl)amino]-8-methoxy-N-[1-(phenyimethyl)-4-piperidinyl]-3-quinolinecarboxamide: A mixture of 4-[(4-formylphenyl)amino]-8-methoxy -3-quinolinecarboxylic acid (5.34 g, 16.6 mmol), 1-(3-dimethylamino--propyl) 3-ethylcarbodiimide hydrochloride (4.79 g, 25 mmol), 1-hydroxybenzotriazole monohydrate (2.70 g, 20 mmol), triethylamine (5.06 g, 50 mmol), and 4-amino-1- benzylpiperidine (3.16 g, 16.6 mmol) was suspended in dry DMF (80 mL) and heated at 60° C. for 4 hours under nitrogen. After dilution with methylene chloride, the reaction mixture was extracted with 1N NaOH (aq) and water (2X). The dried (MgSO$_4$) organic phase was evaporated to a residue (7.9 g, 16 mmol). The product was purified by flash column chromatography on silica gel (125:1 loading ratio; methylene chloride/methanol, 95/5 eluant) which afforded 7.5 g (15.2 mmol, 91% yield) of the product as an amber oil: $^1$H NMR (Me$_2$SO-d$_6$, 200 MHz) δ 9.76 (s, 1 H), 9.55 (s, 1 H), 8.82 (s, 1 H), 8.40 (d, 1 H), 7.78 (d, 2 H), 7.64 (d, 1 H), 7.50 (t, 1 H), 7.27 (m, 6 H), 6.96 (d, 2 H), 3.98 (s, 3 H), 3.50 (m, 1 H), 3.40 (m, 2 H), 2.67 (d, 2 H), 1.93 (t, 2 H), 1.51 (d, 2 H), 1.34 (q, 2 H).

Step 3, 4-[[4-[[(1-Butyl-4-piperidinyl)amino]methyl]-phenyl]amino]-8-methoxy -N-[1-(phenyimethyl)-4-piperidinyl]-3-qinolinecarboxamide: A mixture of 4-[(4formylphenyl)amino]-8-methoxy-4-quinolinecarboxylic acid (7.5 g, 15 mmol), 4-amino-1-butylpiperidine (2.34 g, 15 mmol), and 4-toluenesulfonic acid monohydrate (2.85 g, 15 mmol) was refluxed in toluene (500 mL) for 3 hours with azotropic removal of water. The solvent volume was reduced by distillation and the stirred reaction mixture diluted with methanol then treated with an excess of solid sodium borohydride at room temperature. The solvent was removed *in vacuo*, the residue redissolved in methylene chloride and extracted with 1N NaOH (aq) and water (2X). The dried (MgSO$_4$) organic phase was evaporated to a yellow oil (8.5 g, 13.4 mmol). The product was purified by flash column chromatography on silica gel (100:1 loading ratio, 10% methanol-methylene chloride saturated with ammonia gas eluant) and afforded, after drying *in vacuo* overnight, 2.6 g (4.1 mmol, 27% yield) of the title product as a yellow amorphous solid: m.p. 85°–90° C.; $^1$H NMR (Me$_2$SO-d$_6$, 400 MHz) δ 9.51 (s, 1 H), 8.73 (s, 1 H), 8.36 (d, J=7.6 Hz, 1 H), 7.53 (dd, J=7.8, 0.8 Hz, 1 H), 7.32 (t, J=7.7 Hz, $^1$H), 7.26 (m, 5 H), 7.14 (d, J=7.0 Hz, $^1$H), 7.13 (d, J=8.4 Hz, 2 H), 6.83 (d, J=8.4 Hz, 2 H), 3.93 (s, 3 H), 3.60 (s, 3 H), 3.52 (m, 1 H), 3.40 (s, 2 H), 2.71 (bd, 4 H), 2.30 (m, $^1$H), 2.18 (t, J=7.1Hz, 2 H), 1.92 (t, J=11.5 Hz, 2 H), 1.79 (t, J=10.5 Hz, 2 lt), 1.72 (d, J=12.7 Hz, 2 H), 1.58 (d, J=8.9 Hz, 2 H), 1.40 (q, J=11.0 Hz, 2 H), 1.35 (p, J=8.3 Hz, 2 H), 1.24 (sextet, J=7.8 Hz, 2 H), 1.22 (q, J=10.9 Hz, 2 H), 0.85 (t, J=7.2 Hz, 3 H); MS (+FAB), m/z (rel. intensity) =635 (MH+, 15), 479 (20); IR (KBr) 3250, 2930, 2800, 2760, 1630, 1590, 1505, 1265, 1210, 1060, 930, 780, 740, 700 cm$^{-1}$.

Anal. Calcd. for C$_{39}$H$_{50}$N$_6$O$_2$: C, 73.78; H, 7.94; N, 13.24.

Found: C, 73.43; H, 8.00; N, 12.85.

EXAMPLE 8

N-(1-Butyl-4-piperidinyl)-8-methoxy-4-[[4-[[[1-(phenylmethyl) -4-piperidinyl]amino]carbonyl]phenyl]amino]-3-quinolinecarboxamide N-( 1-Butyl-4-piperidinyl)-8-methoxy-4-[[4-[[[1-(phenylmethyl)-4-piperidinyl]amino]carbonyl]phenyl]amino]-3-quinolinecarboxamide was prepared as a hygroscopic material (0.215 hydrate) by coupling 8-methoxy-4-[[4-[[[1-(phenylmethyl)-4-piperidinyl]amino]carbonyl]phenyl]amino]-3-quinolinecarboxylic acid and 4-amino-1-butylpiperidine as described for Example 17, Step 5. 4-Amino -1-butyl-piperidine can be prepared from 4-bromobutane and 1,4-dioxa-8-azaspiro[4.5]-decane as described in U.S. Pat. Nos. 3,875,165 and 4,816,464: mp 215°–220 ° C.; $^1$H NMR (Me$_2$SO-d$_6$, 400 MHz) δ 9.50 (s, 1 H), 8.77 (s, 1 H), 8.39 (d, J=7.5 Hz, 1 H), 8.01 (d, J=7.8 Hz, 1 H), 7.70 (d, J=8.6 Hz, 2 H), 7.57 (d, J=8.4 Hz, 1 H), 7.41 (m, 1 H), 7.18–7.32 (m, 6 H), 6.88 (d, J=8.6 Hz, 2 H), 3.95 (s, 3 H), 3.72–3.76 (m, 1 H), 3.44–3.49 (m, 3 H), 2.68–2.80 (m, 4 H), 2.14–2.19 (m, 2 H), 1.95–2.01 (m, 2 H), 1.71–1.83 (m, 4 H), 1.53–1.60 (m, 4 H), 1,1-1.4 (m, 6 H), 0.8 (t, J=7.24 Hz, 3 H); Karl Fischer, 0.58% H$_2$O.

Anal. Calcd for C$_{39}$H$_{48}$N$_6$O$_3$.0.215 H$_2$O: C, 71.77; H, 7.48; N, 12.88.

Found: C, 71.57; H, 7.36; N, 13.05.

EXAMPLE 9

N-[1-[6-(Diethylamino )-6-oxohexyl-4-piperidinyl-8-methoxy-4-[[4-[[[1-(phenylmethyl )-4-piperidinyl]amino]carbonyl]phenyl]amino]-3-quinolinecarboxamide Step 1, 6-Bromo-N,N-diethyihexanamide: A solution of 6-bromohexanoyl chloride (100 g, 468 mmol) in 350 ml of tetrahydrofuran was poured into a solution of diethylamine (1.08 moles, 79 g, 112 ml) in 800 ml of rapidly stirring water. The mixture was then extracted with 2×200 ml of CH$_2$Cl2 and the pooled extracts were washed with 250 ml of brine. Drying over Na$_2$SO$_4$ and concentration under reduced pressure afforded 111.6 g (446 mmol, 100% yield) of product as a pale yellow oil: $^1$H NMR (Me$_2$SO-d$_6$, 300 MHz) δ 3.5 (t, J=6.7 Hz, 2 H ), 3.2°–3.3 (m, 4 H ), 2.3 (t, J=7.5 Hz, 2 H ), 1.8 (m, 2 H ), 1.3–1.6 (m, 4 H ), 1.1 (t, J=7.1 Hz, 3 H ), 0.99 (t, J=7.0 Hz, 3 H ).

Step 2, N-[1-[6-(Diethylamino)-6-oxohexyl]-4-piperidinyl]-8-methoxy-4-[[4-[[[1- (phenylmethyl)-4-piperidinyl]amino]carbonyl 1- phenyl]amino]-3-quinolinecarboxamide: N-[1-[6-(Diethylamino)-6-oxohexyl]-4-piperidinyl]-8-methoxy-4-[[4-[[[1-(phenylmethyl)-4-piperidinyl]amino]carbonyl]-phenyl]amino]-3-quinolinecarboxamide was prepared as a hygroscopic solid (1.14 hydrate) by coupling 8-methoxy-4-[[4-[[[1-(phenylmethyl)-4-piperidinyl]amino]-carbonyl]phenyl]amino]-3-quinolinecarboxylic acid and 4-amino-N,N-diethylol-piperidinehexanamide as described for Example 17, Step 5. 4-amino-N,N-diethyl-1-piperidinehexanamide can be prepared from 6-bromo-N,N-diethylhexanamide (Step 1) and 1,4-dioxa-8-azaspiro[4.5]-decane as described in U.S. Pat. Nos. 3,875,165 and 4,816,464: mp 115°–120° C.; $^1$H NMR (Me$_2$SO-d$_6$, 400 MHz) δ 9.49 (s, 1 H), 8.77 (s, 1 H), 8.39 (d, J=7.5 Hz, 1 H), 8.00 (d, J=7.7 Hz, 1 H), 7.69 (d, J=8.7 Hz, 2 H), 7.56 (d, J=1 H) 7.40 (m, 1 H), 7.1–7.3 (m, 6 H), 6.87 (d, J=8.68 Hz, 2 H), 3.95 (s, 3 H), 3.7 (m, 1 H), 3.1–3.6 (m, 7 H), 2.6–2.9 (m, 4 H), 2.1–2.3 (m, 4 H), 1.98 (t, J=11.0 Hz, 2 H), 1.65–1.85 (m, 4 H), 1,1–1.6 (m, 12 H), 0.95–1.1 (doft, J=7.1Hz, 6H); Karl Fischer, 2.63% H$_2$O Anal. Calcd for C$_{45}$H$_{59}$N$_7$O$_4$.1.14 H$_2$O: C, 69.07; H, 7.89; N, 12.53.

Found: C, 69.26; H, 7.88; N, 12.57.

EXAMPLE 10

4-[[4-[[(1-Butyl-4-piperidinyl)(1-oxobutyl)amino]methyl]phenyl]-amino[-8-methoxy-N-[1-(phenylmethyl)-4-piperidinyl]-3-quinoline-carboxamide 4-[[4-[[(1-Butyl-4-piperidinyl)amino]methyl]phenyl]amino]-8-methoxy-N -[1-(phenylmethyl)-4-piperidinyl]-3-quinolinecarboxamide (1.7 g, 2.68 mmol) and butyric anhydride (0.47 g, 3.0 mmol), dissolved in dry THF (15 mL), was treated dropwise with a solution of triethylamine (0.30 g, 3.0 mmol) in THF. The mixture was stirred for 2 hours at room temperature and concentrated *in vacuo*. The residue was redissolved in methylene chloride (150 mL) and extracted with 1N (NaOH (aq) (2×50 mL) and water (3×50 mL). The dried (MgSO$_4$) organic phase was evaporated *in vacuo* to yield 1.3 g (1.8 mmol, 67%) of an amber oil. The product was purified by flash column chromatography on silica gel (100:1 loading ratio, 95/5 methylene chloride-methanol eluant) and afforded, after drying *in vacuo* for 48 hrs, 0.60 g (0.85 mmol, 32% yield) of the title product as a yellow amorphous solid: m.p. 113°–115° C.; $^1$H NMR (Me$_2$SO-d$_6$, 400 MHz), a 1:1 mixture of amide rotamers, a: b) δ 9,45 (s, 1Ha), 9.32 (s, 1Hb), 8.71 (s, 1Ha), 8.69 (s, 1Hb), 8.32 (d, 2Ha), 8.25 (d, 2Hb), 7.62 (d, 1Hb), 7.54 (d, 1Ha), 7.28 (m 6 H), 7.15 (d, 1Hb), 7.12 (d, 1Ha), 6.99 (m, 2H), 6.89(d,J=8.3Hz, 2Hb), 6.81 (d,J=8.3Hz, 2Ha), 4.41 (s, 2Hb), 4.38(s, 2Ha), 4.25 (m, 1Hb), 3.92 (s, 3 H), 3.64 (m, 1Ha), 3.46 (m, 1 H), 3.40 (s, 2Ha), 3.38 (s, 2Hb), 2.79 (d, J=11.0 Hz 2 H), 2.67 (m, 2 H), 2.37 (t, 2Ha), 2.17 (m, 2 H), 2.11 (t, 2Hb), 1.88 (m, 4 H), 1.20–1.57 (m, 14 H), 0.89 (t, J=7.2 Hz, 3Ha), 0.83 (t, J=7.2Hz, 3Ha), 0.82 (t, J=7.1 Hz, 3Hb), 0.76 (t, J=7.2 Hz, 3Hb); MS (+FAB), m/z (rel. intensity)=705 (MH$^+$, 25), 479(s), 289(40), 172(60), 138(60), 91(100); IR (KBr) n: 3280, 2940, 2920, 2790, 2750, 1630, 1585, 1495, 1400, 1260, 1210, 1055, 920, 780, 735, 690 cm$^{-1}$ Anal. Calcd. for C$_{43}$H$_{56}$N$_6$O$_3$: C, 73.26; H, 8.01; N, 11.92.

Found: C, 72.90; H, 7.97; N, 11.89

EXAMPLE 11

N-[1-[4-[(Diethylamino)carbonyl]phenyl-4-piperidinyl-8-methoxy-4-[[4-[[[1-(phenylmethyl )-4-piperidinyl]amino]carbonyl]phenyl]amino ]-3-quinolinecarboxamide Step 1, 3-(Chloromethyl)-N,N-diethylbenzamide: A sohtion of 3-(chloromethyl)benzoyl chloride (50 g, 264 mmol) in 200 ml of tetrahydrofuran was poured into a solution of diethylamine (607 mmol, 44.4 g, 63.1 ml) in 450 ml of rapidly stirring water. After 10 m, the mixture was extracted with 100 ml of ether and the extract was dried over MgSO$_4$ and concentrated under recuced pressure affording 53.23 g (236 mmol, 89% yield) of the product as a clear oil.

Step 2, N-[1-[4-[(Diethylamino)carbonyl]phenyl]-4-piperidinyl]-8-methoxy -4-[[4-[[[1-(phenylmethyl )-4-piperidinyl]amino]carbonyl] phenyl]-amino]-3-quinolinecarboxamide: N-[1-[4-[(Diethylamino)-carbonyl]-phenyl]-4-piperidinyl]-8-methoxy-4-[[4-[[[1-(phenylmethyl)-4-pipeddinyl]amino]-carbonyl]-phenyl-]amino]-3-quinolinecarboxamide was prepared as a hygroscopic solid (0.88 hydrate) by coupling 8-methoxy-4-[[4-[[[1-(phenylmethyl)-4-piperidinyl]amino]-carbonyl]phenyl]amino]-3-quinolinecarboxylic acid and 3-[(4-amino-1piperidinyl)methyl]-N,N-diethylbenzamide as described for Example 17, Step 5. 3-[(4-Amino-1-piperidinyl)methyl]-N,N-diethylbenzamide can be prepared from 3-(Chloromethyl)-N,N-diethylbenzamide (Step 1 ) and 1,4-dioxa-8-azaspiro[4.5]-decane as described in U.S. Pat. Nos. 3,875,165 and 4,816,464: :top 134°–140 ° C.; $^1$H NMR (Me$_2$SO-d$_6$, 400 MHz) δ 9.48 (s, 1 H), 8.76 (s, 1 H), 8.40 (d, J=7.6 Hz, 1 H), 7.99 (d, J=7.8 Hz, 1 H), 7.68 (d, J=8.7 Hz, 2 H), 7.57 (d, J=8.6 Hz, 1 H), 7.41 (m, 1 H), 7.13–7.36 (m, 10 H), 6.87 (m, J=8.7 Hz, 2 H), 3.94 (s, 3 H), 3.7 (m, 1 H), 3.3–3.6 (m, 7 H), 3.1 (m, 2 H), 2.6–2.9 (m, 4 H), 1.8–2.1 (m, 4 H), 1.3–1.8 (m, 8 H), 0.9–1.2 (m, 6 H); Karl Fischer, 1.97% H$_2$O Anal. Calcd for C$_{47}$H$_{55}$N$_7$O$_4$.0.88 H$_2$O: C, 70.76; H, 7.17; N, 12.29

Found: C, 70.17; H, 7.34; N, 11.96.

EXAMPLE 12

N-[1-(2-Phenylethyl)-4-piperidinyl]-8-methoxy-4-[[4-[[[1-(phenylmethyl)-4-piperidinyl]amino]carbony]-phenyl]amino]-3-quinolinecarboxamide N-[1-(2-Phenylethyl)-4-piperidinyl]-8-methoxy-4-[[4-[[[1-(phenylmethyl) -4piperidinyl]amino]carbonyl]-phenyl]amino]-3-quinolinecarboxamide was prepared by coupling 8-methoxy-4-[[4-[[[1-(phenylmethyl)-4-piperidinyl]amino]carbonyl]phenyl]amino]-3-quinolinecarboxylic acid and 1-phenethyl-4-aminopiperidine as described for Example 17, Step 5. 1-phenethyl-4-aminopiperidine can be prepared from 1-phenethyl-4-piperidone as described in U.S. Pat. No. 3,875,165: mp 216°–220 ° C.; $^1$H NMR (Me$_2$SO-d$_6$, 400 MHz) δ 9.51 (s, 1 H), 8.79 (s, 1 H), 8.40 (d, 5=7.7 Hz, 1 H), 8.00 (d, J=7.7 Hz, 1 H), 7.71 (d, J=8.7 Hz, 2 H), 7.57 (d, J=8.5 Hz, 1 H), 7.41 (m, 1 H), 7.10–7.35 (m, 11 H), 6.88 (d, J=8.7 Hz, 2 H), 3.93 (s, 3 H), 3.7–3.8 (m, 1 H), 3.4–3.6 (m, 3 H), 2.6–2.9 (m, 6 H), 2.4–2.5 (m, 2 H), 1.85–2.10 (m, 4 H, 1.7–1.8 (m, 2 H), 1.5–1.7 (m, 4 H), 1.3–1.5 (m, 2 H).

Anal. Calcd for C$_{43}$H$_{48}$N$_6$O$_3$: C, 74.11; H, 6.94; N, 12.06

Found: C, 73.82; H, 6.97; N, 12.02.

EXAMPLE 13

4-[[4-[[(1-Butyl-4-piperidinyl)amino]carbonyl]phenyl-]amino]-8-methoxy-N-[1-(phenylmethyl)-4-piperidinyl]]-3-quinoinecarboxamide 4-[[4-[[(1-Butyl-4-piperidinyl)amino]carbonyl]-phenyl]amino]-8-methoxy -N[1-(phenylmethyl)-4-piperidinyl]-3-quinolinecarboxamide 0.17 dichloromethane hemi-hydrate can be prepared by the procedure of Example 3: mp 254°–256 ° C.; $^1$H NMR (Me$_2$SO-d$_6$, 400 MHz) δ 9.48 (s, 1 H), 8.76 (s, 1 H), 8.39 (d, J=7.6 Hz, 1 H), 7.96 (d, J=7.8 Hz, 1 H), 7.68 (d, J=8.6 Hz, 2 H), 7.57 (d, J=8.6 Hz, 1 H), 7.40 (t, J=8.4 Hz, 1 H), 7.25 (m, 5 H), 7.19 (d, J=7.8 Hz, 1 H), 6.87 (d, J=8.6 Hz, 2 H), 3.94 (s, 3 H), 3.69 (bm, 1 H), 3.49 (bm, 1 H), 3.38 (s, 2 H), 2.81 (d, J=11.3 Hz, 2 H), 2.67 (d, J=11.3 Hz, 2 H), 2.22 (t, J=7.4 Hz, 2 H), 1.88 (m, 4 H), 1.68 (d, J=10.2 Hz, 2 H), 1.51 (m, 4 H), 1.38 (m, 4 H), 1.26 (p, J=7.7 Hz, 2 H), 0.86 (t, J=7.3 Hz, 3 H); Karl Fischer, 1.34% H$_2$O Anal. Calcd for C$_{39}$H$_{48}$N$_6$O$_3$.0.5 H$_2$O.0.17 CH$_2$Cl$_2$: C, 69.98; H, 7.40; N, 12.50

Found: C, 70.24; H, 7.30; N, 12.59.

EXAMPLE 14

8-Methoxy-N-(1-methyl-4-piperidinyl)-4-[[4-[[[1-(phenylmethyl)-4-piperidinyl]amino]carbonyl]-phenyl]amino]-3-quinolinecarboxamide 8-Methoxy-N-(1-methyl-4-piperidinyl)-4-[[4-[[[1-(phenylmethyl)-4-piperidinyl]amino]carbonyl]phenyl-]amino]-3-quinolinecarboxamide was prepared by coupling 8-methoxy-4-[[4-[[[1-(phenylmethyl)-4-piperidinyl]amino]carbonyl]phenyl]amino]-3-quinolinecarboxylic acid and commercially available 1-methyl-4-(methylamino)piperidine as described for Example 17, Step 5: mp 230°–232 ° C.; $^1$H NMR (Me$_2$-SO-d$_6$, 400 MHz), 3:1 mixture of amide rotamers, a:b) δ 9.09 (s, 1Ha), 8.84 (s, 1Hb), 8.58 (s, 1Hb), 8.51 (s, 1Ha), 7.98 (d, J=7..9 Hz, 1Ha), 7.93 (d, J=7.9 Hz, 1Hb), 7.78 (d, J=8.7 Hz, 2Hb), 7.71 (d, J=8.7 Hz, 2Ha), 7.65 (d, J=8.3 Hz, 1 H), 7.51 (t, J=8.5 Hz, 1 H), 7.43 (m, 5Hb), 7.30 (m, 5Ha), 7.24 (d, J=7.5 Hz, 1 H), 6.91 (d, J=8.7 Hz, 2Ha), 6.77 (d, J=8.7 Hz, 2Hb), 3.96 (s, 3 H), 3.74 (m, 2 H), 3.46 (s, 2 H), 3.32 (b, 2 H), 2.80 (d, J=11.6 Hz, 4Ha), 2.69 (s, 3Hb), 2.64 (d, J=12.2 Hz, 4Hb), 2.58 (s, 3Ha), 2.06 (s, 3Ha), 2.00 (t, J=13.9 Hz, 2 H), 1.97 (s, 3Hb), 1.72 (m, 4 H), 1.56–1.59 (m, 4 H).

Anal. Calcd for $C_{37}H_{44}N_6O_3$: C, 71.59; H, 7.14; N, 13.54.

Found: C, 71.88; H, 7.10; N, 13.90.

EXAMPLE 15

N-[1-[(3-Methoxyphenyl)methyl[-4-piperidinyl-8-methoxy-4-[[4-[[[1-(phenylmethyl)-4-piperidinyl-]amino]carbonyl]phenyl]amino-3-quinolinecarboxamide N-[1-[(3-Methoxyphenyl)methyl]-4-piperidinyl]-8-methoxy-4-[[4-[[[1-(phenylmethyl)-4-piperidinyl-]amino]carbonyl]phenyl]amino]-3-quinoline-carboxamide was prepared as a hygroscopic solid (0.76 hydrate) by coupling 8-methoxy-4 -[[4-[[[1-(phenylmethyl)-4-piperidinyl]amino]carbonyl]phenyl]amino]-3-quinolinecarboxylic acid and 1-[(3-methoxyphenyl)methyl]-4-piperidinamine as described for Example 17, Step 5. 1-[(3-Methoxyphenyl)methyl]-4-piperidinamine can be prepared from 3-methoxybenzyl chloride and 1,4-dioxa-8-azaspiro[4.5]-decane as described in U.S. Pat. Nos. 3,875,165 and 4,816,464: mp 135°–142° C.; $^1$H NMR ($Me_2SO-d_6$, 400 MHz) δ 9.48 (s, 1 H), 8.76 (s, 1 H), 8.39 (d, J=7.5 Hz, 1 H), 7.98 (d, J=7.7 Hz, 1 H), 7.68 (d, J=8.6 Hz, 2 H), 7.57 (d, J=8.6 Hz, $^1$H), 7.41 (m, $^1$H), 7.10–7.35 (m, 8 H), 6.7–6.9 (m, 4 H), 3.94 (s, 3 H), 3.6–3.8 (m, 4 H), 3.2–3.6 (m, 5 H), 2.6–2.9 (m, 4 H), 1.3–2.1 (m, 12 H); Karl Fischer, 0.76 moles of $H_2O$.

Anal. Calcd for $C_{43}H_{48}N_6O_4 \cdot 0.76\ H_2O$: C, 71.09; H, 6.87; N, 11.57

Found: C, 70.90; H, 6.89; N, 11.86.

EXAMPLE 16

8-Methoxy-4-[[4-[[[1-(phenylmethyl)-4-piperidinyamino]-carbonyl]phenl]-amino]1-[[3-(trifluoromethyl)phenyl]methyl]-4-piperidinyl]-3-quinolinecarboxamide 8-Methoxy-4-[[4-[[[1-(phenylmethyl)-4-piperidinyl-]amino]carbonyl]phenyl]amino]-1-[[3-(trifluoromethyl)-phenyl]methyl]-4-piperidinyl]-3-quinolinecarboxamide was prepared as a hygroscopic solid (0.46 hydrate) by coupling 8-methoxy-4-[[4-[[[1-(phenylmethyl)-4-piperidinyl]amino]carbonyl]phenyl]amino]-3-quinolinecarboxylic acid and 1-[[3-(trifluoromethyl)-phenyl]methyl]-4-piperidinamine as described for Example 17, Step 5. 1-[[3-(trifluoromethyl)phenyl]methyl]-4-piperidinamine can be prepared from 3-(triflouromethyl)benzyl chloride and 1,4-dioxa-8-azaspiro[4.5]-decane as described in U.S. Pat. Nos. 3,875,165 and 4,816,464: mp 132°–138° C.; $^1$H NMR ($Me_2SO-d_6$, 400 MHz) δ 9.48 (s, 1 H), 8.76 (s, 1 H), 8.39 (d, J=7.6 Hz, 1 H), 7.97 (d, J=7.8 Hz, 1 H), 7.68 (d, J=8.7 Hz, 2 H), 7.10–7.65 (m, 12 H), 6.87 (d, J=8.7 Hz, 2 H), 3.94 (s, 3 H), 3.62–3.80 (m, 1 H), 3.35–3.60 (m, 5 H), 2.6–2.9 (m, 4 H), 1.95 (m, 4 H), 1.3–1.8 (m, 8 H); Karl Fischer, 0.46 moles of $H_2O$.

Anal. Calcd for $C_{43}H_{45}F_3N_6O_3 \cdot 0.46\ H_2O$: C, 68.03; H, 6.10; N, 11.07.

Found: C, 68.25; H, 6.45; N, 11.15.

EXAMPLE 17

7-Chloro-N-[1-(phenylmethyl)-4-piperidinyl]-4-[[4-[[[1-(phenylmethyl)-4-piperidinyl]amino]carbonyl]-phenyl]amino]-3-quinolinecarboxamide Step 1, 4,7-dichloro-3-quinolinecarboxylic acid ethyl ester: 7-Chloro-1,4-dihydro-4-oxo-3-quinolinecarboxylic acid ethyl ester [76.0 g, 302 mmol, prepared as described by C. C. Price et al in J. Am. Chem. Soc., 68, 1204 (1946)]was refluxed for 4.5 h in 310 ml of $POCl_3$. The resulting black solution was then concentrated in vacuo and the residue was dissolved in 100 ml of acetone. It was poured onto 1 kg of ice and brought to pH 7 with 50% NaOH. The mixture was then extracted with 3×125 ml of $CH_2Cl_2$ and the pooled extracts were dried over $Na_2SO_4$ and concentrated to a black solid that was dried in vacuo overnight affording 74.7 g (276 mmol, 92% crude yield) of 4,7-dichloro-3-quinolinecarboxylic acid ethyl ester that was used in the next step without purification.

Step 2, 4-[(4-Carboxyphenyl)amino]-7-chloro-3-quinolinecarboxylic Acid ethyl ester hydrochloride: 4,7-Dichloro-3-quinolinecarboxylic acid ethyl ester (72.0 g, 267 mmol) and p-aminobenzoic acid (36.6 g, 267 mmol) were refluxed in 675 ml of THF for 6 h then cooled to room temperature. The yellow precipitate was filtered, combined with the product from a 10 mmol reaction and washed with THF, then ether. The yellow powder was then dried in vacuo overnight affording 82.7 g (203 mmol, 73% yield) of 4-[(4-carboxyphenyl)amino]-7-chloro-3-quinolinecarboxylic acid ethyl ester hydrochloride.

Step 3, 7-Chloro-4-[[4-[[[1-(phenylmethyl)-4-piperidinyl]amino]-carbonyl]phenyl]amino]-3-quinolinecarboxylic acid ethyl ester: 4-[(4-Carboxyphenyl)amino]-7-chloro-3-quinolinecarboxylic acid ethyl ester hydrochloride (40.0 g, 98.2 mmol), 1-hydroxybenzotriazole hydrate (16.2 g, 120 mmol) and 1-(3-dimethylaminopropyl)-3-ethylcarbodiimide hydrochloride (24.5 g, 128 mmol) were stirred in 560 ml of DMF and treated with triethylamine (39.8 g, 54.8 ml, 393 mmol) followed by 4-amino-1-benzylpiperidine (20.6 g, 22.0 ml, 108 mmol). The reaction mixture was heated at 85° C. for 3.5 h, poured into 1.3 L of $CH_2Cl_2$ and washed with 3×500 ml of water. The organic phase was dried over $Na_2SO_4$ and concentrated in vacuo for 3 days. This afforded 51.7 g (95.2 mmol, 97% yield) of 7-chloro-4-[[4 -[[[1-(phenylmethyl)-4-piperidinyl]amino]carbonyl]phenyl]amino]-3-quinolinecarboxylic acid ethyl ester as a yellow solid.

Step 4, 7-Chloro-4-[[4-[[[1-(phenylmethyi)-4-piperidinyl]amino]-carbonyl]phenyl]amino]-3-quinolinecarboxylic acid: 7-Chloro-4-[[4-[[[1-(phenylmethyl)-4piperidinyl]amino]carbonyl]phenyl]amino]-3-quinolinecarboxylic acid ethyl ester (51.7 g, 95.2 mmol) was stirred in 550 ml of methanol and treated with 133 ml of 2.5 M NaOH. The reaction mixture was then refluxed for 45 m at which point the hot homogeneous solution was treated with 166 ml of 2 M HCl to precipitate the product. After the mixture cooled to room temperature, the product was filtered and washed with water, methanol and then ether. The yellow powdery material was then dried in vacuo overnight affording 31.3 g (60.9 mmol, 64% yield) of 7-chloro-4-[[4-[[[1-(phenylmethyl)-4-piperidinyl]amino]carbonyl]phenyl-]amino]-3-quinolinecarboxylic acid.

Step 5, 7-Chloro-N-[1-(phenylmethyl)-4-piperidinyl]-4-[[4-[[[1-(phenylmethyl) -4-piperidinyl]]amino]carbonyl]phenyl]amino]-3-quinolinecarboxamide: 7-Chloro -4-[[4-[[[1-(phenylmethyl)-4-piperidinyl]amino]-carbonyl]phenyl]amino]-3-quinolinecarboxylic acid (2.00 g, 3.88 mmol), 1-hydroxybenzotriazole hydrate (0.640 g, 4.74 mmol) and 1-(3-dimethylaminopropyl)-3-ethylcarbodiimide hydrochloride (0.968 g, 5.05 mmol) were stirred in 22 ml of DMF and treated with triethylamine (1.57 g, 2.2 ml, 15.5 mmol) followed by 4-amino-1-benzylpiperidine (0.813 g, 0.87 ml, 4.27 mmol). The reaction mixture was then heated at 90° C. under nitrogen for 4 h, cooled to room temperature and poured into 250 ml of $CH_2CH_2$. The solution was then washed with 3×200 ml of water and concentrated under reduced pressure to a pale beige powder that was dried in vacuo overnight affording 2.037 g (2.96 mmol, 76% yield) of 7-Chloro-N-[1-(phenylmethyl)-4-piperidinyl]-4-[[4-[[[1-(phenylmethyl) -4-piperidinyl]amino]-carbonyl]phenyl]amino]-3-quinolinecarboxamide: mp 230.5°-232° C.; IR (KBr) 3440, 3330, 30 30, 2950, 2800, 1630 cm$^{-1}$; $^1$H NMR (Me$_2$SO-d$_6$, 400 MHz) δ 9.7 (s, 1 H), 8.8 (s, 1 H), 8.39 (d, J=7.5 Hz, 1 H), 8.11 (d, J=9.1 Hz, 1 H), 8.0 (m, 2 H), 7.7 (d, J=8.7 Hz, 2 H), 7.6 (d of d, J=2.2, 9.1 Hz, 1 H), 7.1-7.35 (m, 10 H), 6.9 (d, J=8.7 Hz, 2 H), 3.7 (m, 1 H), 3.4 (m, 5 H), 2.74°-2.82 (m, 2 H), 2.64-2.7 (m, 2 H), 1.84-2.04 (m, 4 H), 1.64°-1.72 (m, 2 H), 1.46-1.58 (m, 4 H), 1.3-1.4 (m, 2 H); MS (+DCI, isobutane) m/z (rel intensity)=687 (M+, 100).

Anal. Calcd for $C_{41}H_{43}ClN_6O_2$: C, 71.65; H, 6.31; N, 12.23

Found: C, 71.62; H, 6.27; N, 12.35.

PHARMACOLOGICAL PROCEDURE

1. Bradykinin Receptor Binding Assay

The following procedure is used to identify compounds which compete specifically with triturated bradykinin ($^3$H-BK) for BK$_2$ receptor sites in guinea pig ileum.

The distal portion of adult, male guinea pig (Hartley strain, 350-500 g, Charles River) ileum is removed and placed in ice cold homogenization buffer [25 nM N-tris (hydroxymethyl)methyl-2-aminoethane sulfonic acid (TES), 1 mM 1, 10-phenanthroline, adjusted to pH 6.8 with ammonium hydroxide].

The contents of the ileal lumen are rinsed out with cold homogenization buffer. The tissue is cut into small pieces and homogenized in 20 volumes of homogenization buffer 3 times of 10 seconds duration using a Brinkman Polytron homogenizer equipped with a PTA 10 TS generator at setting 5.

The homogenate is fillered through a surgical gauze sponge and centrifuged at 50,000 × g for 20 minutes at 4° C. The supernatant fluid is discarded and the homogenization and centrifugation procedures are repeated. After discarding the supernatant fluid, the final pellet is resuspended in 40 volumes of assay buffer (25 mM TES, pH 6.8, 1 mM 1,10-phenanthroline, 1 mM dithiothreitol, 2 μM captopril, 140 μg/ml bacitracin and 0.1% bovine serum albumin (BSA)). The homogenate is filtered once more through a surgical gauze sponge and kept on ice until used. The assay is performed using only polypropylene pipet tips and polypropylene test tubes. Each tube receives 100 μl of 800 pM $^3$H-BK, 100 μl of the test compound solution (100 μM) or vehicle (assay buffer), and 100 μl of 25 mg/ml tissue homogenate in a total volume of 1 ml. The final concentration of 3H-BK is 80 pM. The final tissue concentration is 2.5 mg/ml. Compounds are screened at 100 μM. Compounds which are not soluble in water are first solubilized in DMSO and then diluted 1:100 in the assay buffer. Addition of 100 μl of this sample to the assay will yield a final DMSO concentration of 0.1% which has been shown not to affect the binding assay. Nonspecific binding is determined in the presence of 1 μM unlabeled bradykinin. All determinmions are made in triplicate. Three 100 μl aliquots of the 800 pM 3H-BK working solution are added directly to scintillation vials to determine the total added radioactivity.

The tubes are incubated for 90 minutes at 25° C. while being gently agitated on an orbital shaker. Bound ligand is separated from free ligand, using Whatman GF/B glass fiber filters (pretreated with 0.1% aqueous polyethyleneimine made neutral with HCl). A Brandel receptor binding harvester is used. Assay tubes and glass fiber filters are rinsed three times with 3 ml of cold physiological saline.

The filter discs are transferred to 20 ml scintillation vials. Ten ml of aqueous sample LSC cocktail (Aquassure, New England Nuclear) is added to each vial. After capping, the vials are agitated for 5 minutes on an orbital shaker. The samples are counted for ten minutes in a refrigerated liquid scintillation counter to obtain the following values: $B_t$ (total binding), $B_{ns}$ (non-specific binding) and $B_x$ (total binding in the presence of the test compound). From these values, control specific binding ($C=B_t-B_{ns}$), specific binding in the presence of the test compound ($D=B_x-B_{ns}$), percent of control (D/C ×100) and percent inhibition $(1-D/C)\times 100$ are calculated.

If 50% inhibition is obtained at the screening concentration, the compound is considered active and a dilution series (typically 1:3 serial dilutions of the test compound) is tested in the binding assay. After calculation of the percent of control of each dilution, the values are analyzed and the IC$_{50}$ with its 95% confidence limits is determined.

2. Bradykinin-induced Writhing in Mice

Male CD-1 Charles River mice (14–19g), fasted overnight but having free access to water, in groups of 10 (control and treated) are given an intraperitoneal (j.p.) injection of 1 mg/kg of prostaglandin PGE$_2$ in phosphate buffered saline (10 μl/g) and after 20 minutes each mouse receives an i.p. injection of bradykinin (0.5 mg/kg in saline). The treatment group of mice receive a test compound either orally 1 hour prior to administration of bradykinin or i.p. 2 minutes prior to administration of bradykinin. Test compounds are given in saline if soluble or as a suspension in 0.5% Tween 80. The percent inhibition of writhing obtained is calculated as follows:

$$\text{Percent inhibition} = \frac{C-D}{C} \times 100$$

where C is the mean number of writhes in the control group and D is the mean number of writhes in the drag group. If 30% inhibition or higher is observed with the screening dose, the test compound is considered active. Several logarithmically spaced doses will be tested and the ED$_{50}$ determined by regression methods with inverse prediction.

Pharmacological Data

| Compound | Bradykinin Binding in G.P. ileum[1] | Bradykinin-induced writhing[2] |
|---|---|---|
| Ex. 1 | 0.430 | |
| Ex. 2 | 0.079 | |
| Ex. 3 | 0.093 | 20 |
| Ex. 4 | 2.7 | |
| Ex. 5 | 2.9 | |
| Ex. 6 | 1.44 | |
| Ex. 7 | (50.5) | |
| Ex. 8 | 1.2 | 32 |
| Ex. 9 | 2.6 | 46 |
| Ex. 10 | (42.8) | |
| Ex. 11 | 1.6 | |
| Ex. 12 | 0.67 | |
| Ex. 13 | 2.9 | |
| Ex. 14 | 1.4 | |
| Ex. 15 | 0.220 | |
| Ex. 16 | 0.25 | |
| Ex. 17 | 0.43 | |
| Ibuprofen | | 43 @ 200 mg/kg p.o. |
| Ketoprofen | | 52 @ 100 mg/kg p.o. |
| Acetaminophen | | 20 @ 300 mg/kg p.o. |
| Morphine | | $ED_{50} = 4.5$ (p.o.) |

[1] $IC_{50}$, μM or (% inhibition at 10 μM)
[2] % inhibition at 30 mg/kg i.p.

PHARMACEUTICAL COMPOSITIONS AND ADMINISTRATION

Compositions for administration to living animals are comprised of at least one of the compounds of Formula I according to the methods of treatment of the invention in association with a pharmaceutical carder or excipient. Effective quantities of the compounds may be administered in any one of various ways, for example, orally as in elixirs, capsules, tablets or coated. tablets, parenterally in the form of sterile solutions, suspensions and in some cases intravenously in the form of sterile solutions, intranasally and to the throat or bronchial region in the form of drops, gargles, syrups, powders, etc. or subcutaneously. Suitable tableting excipients include lactose, potato and maize starches, talc, gelatin, stearic, and silicic acids, magnesium stearate and polyvinyl pyrrolidone.

For the parenteral administration, the carder or excipient can be comprised of a sterile parenterally acceptable liquid, e.g., water or arachis oil contained in ampoules.

Advantageously, the compositions are formulated. as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosages, will of course be determined according to standard medical principles under the direction of a physician or veterinarian. Generally, the following guide to projected human oral dosages is derived by knowledge of the activity obtained in animal screening tests for the various indications in the methods of the invention compared to activity of known agents in the field in the same animal screening tests. However, the amount of the active compounds administered need not be limited by these comparisons due to uncertainty in transposing comparative animal data to human treatments.

Oral dosages projected for analgesia for an adult human are of the order of 1-500 mg/day divided into 2 or 3 closes. Thus, for example, two capsules each containing 1-50 mg active agent of Formula I could be administered 2-3 times daily for pain.

Other routes of administration such as subcutaneous, intraperitoneal, intravenous, etc. are possible with dosage forms being adapted to the situation as will be obvious to one skilled in the an of medicine.

Various modifications and equivalents will be apparent to one skilled in the an and may be made in the compounds, methods of treatment and compositions of the present invention without departing from the spirit or scope thereof, and it is therefore to be understood that the invention is to be limited only by the scope of the appended claims.

What is claimed is:

1. A compound of the formula:

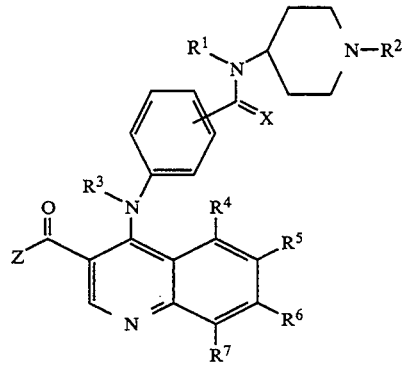

wherein:

$X = O$ or $H_2$;

$R^1 = H$ when $X = O$, or H or $R^{15}CO$ when $X = H_2$;

$R^2 =$ lower alkyl, cycloalkyl, —$(CH_2)_m$-cycloalkyl, —$(CH_2)_m CONR^3 R^3$, or

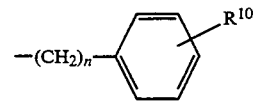

where m is 1 to 10 and n is 1 to 4;

$R^3 = H$ or lower alkyl;

$R^4$, $R^5$, $R^6$ and $R^7$ are independently H, lower alkyl, fluoro, chloro, bromo, iodo, lower alkoxy, or perfluorolower alkyl;

$Z = R^8 N — R^{17}$ where $R^{17}$ is

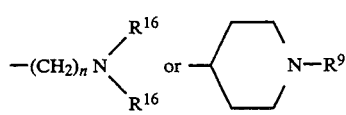

wherein $R^8 = H$, or $R^{16}$ wherein $R^{16}$ is lower alkyl and $R^9 =$ lower alkyl,

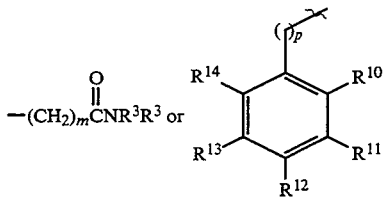

—(CH$_2$)$_m$CNR$^3$R$^3$ or and

P is 1 to 4;

R$^{10}$, R$^{11}$, R$^{12}$, R$^{13}$ and R$^{14}$ are independently H, lower alkyl, fluoro, chloro, bromo, iodo, lower alkoxy, perfluorolower alkyl, —CONR$^{16}$R$^{16}$, —CONHR$^{16}$, —CONH$_2$, NO$_2$, OH, NH$_2$, —NHCONH$_2$, —NR$^3$CONR$^3$R$^3$, or —SO$_y$R$^{16}$ wherein y=0, 1 or 2, R$^{15}$=H, lower alkyl, phenyl, phenylalkyl, perfluorolower alkyl, or —(CH$_2$)$_m$cycloalkyl;

or a pharmaceutically acceptable salt thereof.

2. A compound according to claim 1 having the formula:

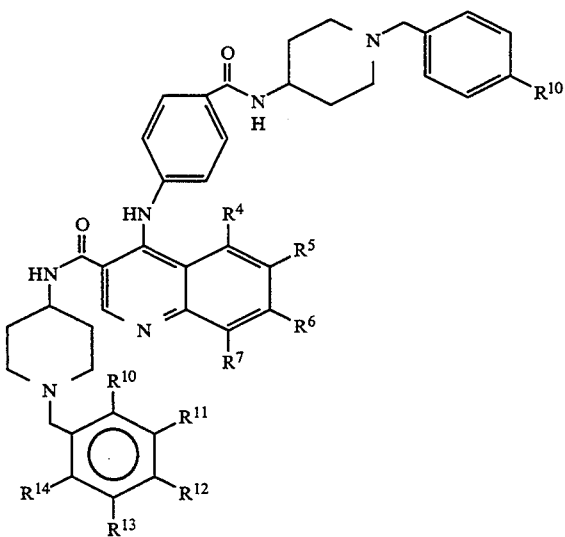

wherein R$^4$, R$^5$, R$^6$ and R$^7$ are independently H, lower alkyl, fluoro, chloro, bromo, iodo, lower alkoxy or perfluorolower alkyl;

R$^{10}$, R$^{11}$, R$^{12}$, R$^{13}$ and R$^{14}$ are independently H, lower alkyl, fluoro, chloro, bromo, iodo, lower alkoxy, perfluorolower alkyl, —CONR$^{16}$R$^{16}$, —CONHR$^{16}$, CONH$_2$, NO$_2$, OH, NH$_2$, NHCONH$_2$, NR$^3$CONR$^3$R$^3$ or SO$_y$R$^{16}$ where y=0, 1 or 2 and R$^3$ is H or lower alkyl and R$^{16}$ is lower alkyl;

or a pharmaceutically acceptable salt thereof.

3. A compound according to claim 1 which is N-[1-[4-(1,1-dimethylethyl)phenyl]methyl]-4-piperidinyl]-8-methoxy-4-[[4-[[[1-(phenylmethyl)-4-piperidinyl]amino]carbonyl]phenyl]amino]-3-quinolinecarboxamide or a pharmaceutically acceptable salt thereof.

4. A compound according to claim 1 which is N-[1-[(3-chlorophenyl)methyl]-4piperidinyl]-8-methoxy-4-[[4-[[[1-(phenylmethyl)-4-piperidinyl]amino]carbonyl]phenyl]amino]-3-quinolinecarboxamide or a pharmaceutically acceptable salt thereof.

5. A compound according to claim 1 which is 8-methoxy-N-[1-(phenylmethyl) -4-piperidinyl]-4-[[4-[[[1-(phenylmethyl)-4-piperidinyl]amino]carbonyl]phenyl]amino]-3-quinolinecarboxamide or a pharmaceutically acceptable salt thereof.

6. A compound according to claim 1 which is N-[2-(dimethylamino)ethyl]-8-methoxy-4-[[4-[[[1-(phenylmethyl)-4-piperidinyl]amino]carbonyl]phenyl]amino]-3quinolinecarboxamide trifluoroacetate (1:4) or a pharmaceutically acceptable salt thereof.

7. A compound according to claim 1 which is N-[2-(dimethylamino)ethyl]-N -ethyl-8-methoxy-4-[[4-[[[1-(phenylmethyl)-4-piperidinyl]amino]carbonyl]phenyl]amino]-3-quinolinecarboxamide or a pharmaceutically acceptable salt thereof.

8. A compound according to claim 1 which is 4-[[4 -[[[(3-cyclopentyl-1-oxopropyl)[1-[6-(diethylamino)-6-oxohexyl]-4-piperidinyl]amino]methyl]phenyl]-amino]-8-methoxy-N-[1-(phenylmethyl)-4-piperidinyl]-3-quinolinecarboxamide tetrahydrochloride or a pharmaceutically acceptable salt thereof.

9. A compound according to claim 1 which is 4-[[4-[[(1-butyl-4-piperidinyl)amino]methyl]phenyl]amino]-8-methoxy-N-[1-(phenylmethyl)-4-piperidinyl]-3-quinolinecarboxamide or a pharmaceutically acceptable salt thereof.

10. A compound according to claim 1 which is N-(1-butyl-4-piperidinyl)-8 methoxy-4-[[4-[[[1-(phenyhnethyl)-4-piperidinyl]amino]carbonyl]phenyl]amino]-3quinolinecarboxamide or a pharmaceutically acceptable salt thereof.

11. A compound according to claim 1 which is N-[1-[6-(diethylamino)-6oxohexyl]-4-piperidinyl]-8-methoxy-4-[[4-[[[1-(phenylmethyl)-4-piperidinyl]amino]carbonyl]phenyl]amino]-3-quinolinecarboxamide or a pharmaceutically acceptable salt thereof.

12. A compound according to claim 1 which is 4-[[4-[[(1-butyl-4-piperidinyl)(1-oxobutyl)amino]methyl]phenyl]amino]-8-methoxy-N-[1-(phenylmethyl)-4-piperidinyl]-3-quinolinecarboxarnide or a pharmaceutically acceptable salt thereof.

13. A compound according to claim 1 which is N-[1-[4-[(diethylamino)-carbonyl]phenyl]-4-piperidinyl]-8-methoxy-4-[[4-[[[1-(phenylmethyl)-4-piperidinyl]amino]carbonyl]phenyl]amino]-3-quinolinecarboxamide or a pharmaceutically acceptable salt thereof.

14. A compound according to claim 1 which is N-[1-(2-phenylethyl)-4-piperidinyl]-8-methoxy-4-[[4-[[[1-(phenylmethyl)-4-piperidinyl]amino]-carbonyl]-phenyl]amino]-3-quinolinecarboxamide or a pharmaceutically acceptable salt thereof.

15. A compound according to claim 1 which is 4-[[4-[[(1-butyl-4-piperidinyl) -amino]carbonyl]phenyl]amino]-8-methoxy-N-[1-(phenylmethyl)-4-piperidinyl]-3-quinolinecarboxamide 0.17 dichloromethane hemihydrate or a pharmaceutically acceptable salt thereof.

16. A compound according to claim 1 which is 8-methoxy-N-(1-methyl-4-piperidinyl)-4-[[4-[[[1-(phenylmethyl)-4-piperidinyl]amino]carbonyl]phenyl]amino]-3-quinolinecarboxamide or a pharmaceutically acceptable salt thereof.

17. A compound according to claim 1 which is N-[1-[(3-methoxyphenyl)methyl]-4-piperidinyl]-8-methoxy-4-[[4-[[[1-(phenylmethyl)-4-piperidinyl]amino]carbonyl]phenyl]amino]-3-quinolinecarboxamide or a pharmaceutically acceptable salt thereof.

18. A compound according to claim 1 which is 8-methoxy-4-[[4-[[[1-(phenyl-methyl)-4-piperidinyl]amino]carbonyl]phenyl]-amino]-1-[[3-(trifluoromethyl)phenyl]methyl]-4-piperidinyl]-3-quinoline-carboxamide or a pharmaceutically acceptable salt thereof.

19. A compound according to claim 1 which is 7-chloro-N-[1-(phenylmethyl)-4piperidinyl]-4-[[4-[[[1-(phenylmethyl)-4-piperidinyl]amino]carbonyl]phenyl]amino]-3-quinolinecarboxamide or a pharmaceutically acceptable salt thereof.

20. A method of alleviating pain in warm-blooded animals which comprises administration thereto of an effective amount of a compound having the formula:

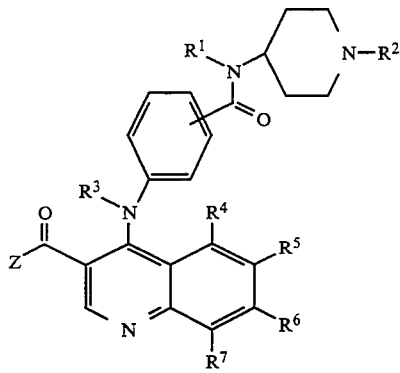

wherein:
X=O or H₂;
R¹=H when X=O, or H or R¹⁵CO when X=H₂;
R²=lower alkyl, cycloalkyl, —(CH₂)ₘ-cycloalkyl; —(CH₂)ₘCONR³R³, or

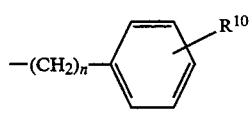

where
m is 1 to 10 and n is 1 to 4;
R³=H or lower alkyl;
R⁴, R⁵, R⁶ and R⁷ are independently H, lower alkyl, fluoro, chloro, bromo, iodo, lower alkoxy, or perfluorolower alkyl;
Z=R⁸N—R¹⁷ where R¹⁷ is

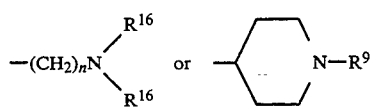

wherein
R⁸=H, or R¹⁶ wherein R¹⁶ is lower alkyl and
R⁹=lower alkyl,

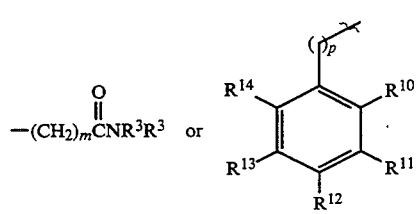

and
P is 1 to 4;
R¹⁰, R¹¹, R¹², R¹³ and R¹⁴ are independently H, lower alkyl, fluoro, chloro, bromo, iodo, lower alkoxy, perfluorolower alkyl, —CONR¹⁶R¹⁶, —CONHR¹⁶, —CONH₂, NO₂, OH, NH₂, —NHCONH₂, —NR³CONR³R³, or —SO_yR¹⁶ wherein y=0, 1 or 2,
R¹⁵=H, lower alkyl, phenyl, phenylalkyl, perfluorolower alkyl, or —(CH₂)ₘcycloalkyl or a pharmaceutically acceptable salt thereof.

21. A pharmaceutical composition for alleviating pain in warm-blooded animals which comprises:
a. an effective amount of a compound having the formula:

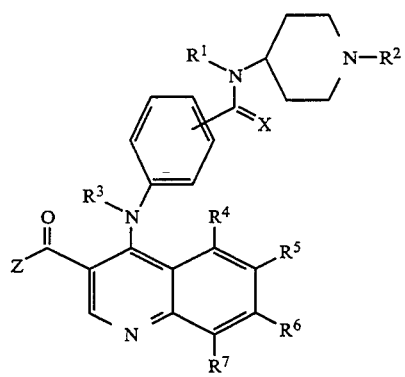

wherein:
X=O or H₂;
R¹=H when X=O, or H or R¹⁵CO when X=H₂;
R²=lower alkyl, cycloalky],—(CH₂)ₘ-cycloalkyl-,—(CH₂)ₘCONR³R³, or

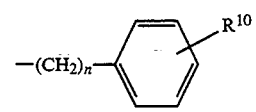

where
m is 1 to 10 and n is 1 to 4;
R³=H or lower alkyl;
R⁴, R⁵, R⁶ and R⁷ are independently H, lower alkyl, fluoro, chloro, bromo, iodo, lower alkoxy, or perfluorolower alkyl;
Z=R⁸N—R¹⁷ where R¹⁷ is

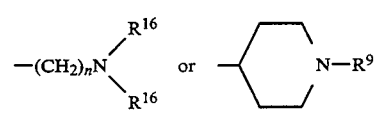

wherein
R⁸=H, or R¹⁶ wherein R¹⁶ is lower alkyl and
R⁹=lower alkyl,

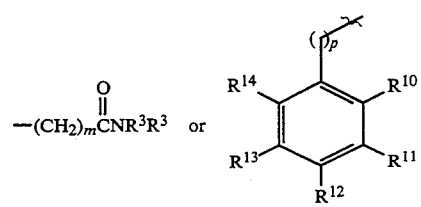

and
P is 1 to 4;

$R^{10}$, $R^{11}$, $R^{12}$, $R^{13}$ and $R^{14}$ are independently H, lower alkyl, fluoro, chloro, bromo, iodo, lower alkoxy, perfluorolower alkyl, —$CONR^{16}R^{16}$, —$CONHR^{16}$, —$CONH_2$, $NO_2$, OH, $NH_2$, —NHCONH$_2$, —NR$^3$CONR$^3$R$^3$, or —SO$_y$R$^{16}$ wherein y=0, 1 or 2, $R^{15}$=H, lower alkyl, phenyl, phenylalkyl, perfluorolower alkyl, or —(CH$_2$)$_m$ cycloalkyl or a pharmaceutically acceptable salt thereof, and, b. a pharmaceutical carrier.

* * * * *